US008184856B2

(12) United States Patent
Smith et al.

(10) Patent No.: US 8,184,856 B2
(45) Date of Patent: May 22, 2012

(54) METHOD AND APPARATUS FOR ASSESSING DRIVER HEAD POSE WITH A HEADREST-MOUNTED RELATIVE MOTION SENSOR

(75) Inventors: Matthew R. Smith, Westfield, IN (US); Gerald J. Witt, Carmel, IN (US); Robert Dufour, Carmel, IN (US)

(73) Assignee: Delphi Technologies, Inc., Troy, MI (US)

( * ) Notice: Subject to any disclaimer, the term of this patent is extended or adjusted under 35 U.S.C. 154(b) by 971 days.

(21) Appl. No.: 12/220,425

(22) Filed: Jul. 24, 2008

(65) Prior Publication Data
US 2008/0288143 A1 Nov. 20, 2008

Related U.S. Application Data

(63) Continuation-in-part of application No. 11/796,807, filed on Apr. 30, 2007, now Pat. No. 7,970,175.

(51) Int. Cl.
*G06K 9/00* (2006.01)
*G06K 9/74* (2006.01)
*B60Q 1/00* (2006.01)
*G08B 23/00* (2006.01)

(52) U.S. Cl. ........ 382/103; 382/104; 382/106; 382/107; 382/321; 340/438; 340/576; 180/271

(58) Field of Classification Search .................. 382/103, 382/104, 106, 107, 321; 340/438, 576; 180/271
See application file for complete search history.

(56) References Cited

U.S. PATENT DOCUMENTS

| | | | | | |
|---|---|---|---|---|---|
| 3,903,514 | A | * | 9/1975 | Mazzola | 340/575 |
| 4,625,329 | A | * | 11/1986 | Ishikawa et al. | 382/104 |
| 4,797,824 | A | * | 1/1989 | Sugiyama et al. | 701/49 |
| 5,322,245 | A | * | 6/1994 | Bassick | 244/122 B |
| 5,694,320 | A | * | 12/1997 | Breed | 701/45 |
| 6,042,145 | A | | 3/2000 | Mitschelen et al. | |
| 6,088,640 | A | | 7/2000 | Breed | |
| 6,154,559 | A | * | 11/2000 | Beardsley | 382/103 |
| 6,184,791 | B1 | * | 2/2001 | Baugh | 340/576 |
| 6,402,195 | B1 | * | 6/2002 | Eisenmann et al. | 280/735 |

(Continued)

FOREIGN PATENT DOCUMENTS
DE 10 2005 101 594 9/2006
(Continued)

OTHER PUBLICATIONS

Beardsley, P.A. "A Qualitative Approach to Classifying Head and Eye Pose." IEEE Workshop on Applications of Computer Vision. (1998): 208-213. Print.*

(Continued)

*Primary Examiner* — Michael A Newman
(74) *Attorney, Agent, or Firm* — Lawrence D. Hazelton

(57) ABSTRACT

A relative motion sensor mounted in the headrest of a vehicle driver seat is used to assess the head pose of a vehicle driver and adjust the headrest position to optimize both the safety of the driver and the sensitivity of the relative motion sensor. At the beginning of each ignition cycle, the relative motion sensor is used to adjust the position of the headrest relative to the driver's head for optimal driver safety, and the relative motion sensor is oriented to provide optimal sensitivity for head pose assessment when the headrest is positioned for driver safety.

8 Claims, 4 Drawing Sheets

U.S. PATENT DOCUMENTS

| | | | |
|---|---|---|---|
| 6,575,902 B1 * | 6/2003 | Burton | 600/300 |
| 7,145,263 B2 | 12/2006 | Nathan et al. | |
| 7,415,126 B2 * | 8/2008 | Breed et al. | 382/100 |
| 2003/0090133 A1 * | 5/2003 | Nathan et al. | 297/217.3 |
| 2004/0122575 A1 * | 6/2004 | Marchthaler | 701/49 |
| 2006/0042851 A1 * | 3/2006 | Herrmann et al. | 180/271 |
| 2007/0086624 A1 | 4/2007 | Breed et al. | |
| 2008/0036186 A1 * | 2/2008 | Schockmel | 280/735 |
| 2008/0111407 A1 | 5/2008 | Szablewski | |
| 2008/0129100 A1 * | 6/2008 | Szablewski | 297/391 |

FOREIGN PATENT DOCUMENTS

WO    WO 2006094760 A1 *   9/2006

OTHER PUBLICATIONS

European Search Report dated Nov. 3, 2009.

* cited by examiner

METHOD AND APPARATUS FOR ASSESSING DRIVER HEAD POSE WITH A HEADREST-MOUNTED RELATIVE MOTION SENSOR

RELATED APPLICATIONS

This application is a continuation-in-part of U.S. patent application Ser. No. 11/796,807, filed Apr. 30, 2007 now U.S. Pat. No. 7,970,175, and assigned to the assignee of this application.

TECHNICAL FIELD

The present invention is relates to driver distraction monitoring in motor vehicles with a relative motion sensor mounted in a headrest of the driver's seat, and more particularly to a method and apparatus for adjusting the headrest position to optimize both the safety of the driver and the sensitivity of the relative motion sensor.

BACKGROUND OF THE INVENTION

Each year numerous automobile accidents are caused by driver distractions, and many of the distractions are visual in nature. For this reason, there has been interest in developing a driver monitoring system for determining if the driver is paying attention to the forward field-of-view. This information can be used to issue an alert if the driver's attention is directed away from the road too long or too often, and possibly to belay other warnings (such as collision-avoidance warnings) if the driver is paying attention to the forward field-of-view. An example of such a monitoring system is Delphi Corporation's Driver State Monitor, which processes a video image of the driver's face to detect and track the driver's eyes for assessing eye gaze. However, detection of facial features such as eyes can be hampered by various kinds of obstructions (including sunglasses) disposed between the video imager and the driver's face. Moreover the distance between the video imager and the driver's face can vary considerably from driver to driver, and it can be difficult to provide adequate controlled illumination of the driver's face. While these drawbacks can be satisfactorily addressed to a large extent by sophisticated processing of the video data, the system cost is frequently too high for most production vehicles due to the combined cost of the imager, optics and signal processor. Accordingly, what is needed is a more cost-effective and yet reliable way of assessing driver head pose.

SUMMARY OF THE INVENTION

The present invention provides an improved method and apparatus for assessing the head pose of a vehicle driver with a relative motion sensor mounted in a headrest of the driver's seat, and for adjusting the headrest position to optimize both the safety of the driver and the sensitivity of the relative motion sensor. At the beginning of each ignition cycle, the relative motion sensor is used to adjust the position of the headrest relative to the driver's head for optimal driver safety, and the relative motion sensor is configured to provide optimal sensitivity for head pose assessment when the headrest is positioned for driver safety.

DESCRIPTION OF THE PREFERRED EMBODIMENT

In general, the present invention is directed to assessment of driver head pose by sensing driver head motion with a headrest-mounted relative motion sensor, where the sensor output is used to position the headrest for optimal driver safety and the sensor is oriented within headrest 12 to provide optimal sensitivity to driver head motion when the headrest is so positioned. The invention is disclosed in the context of a driver distraction system that determines if the driver's attention is forward or non-forward relative to the forward direction of vehicle motion, but the head pose assessment may be directed to other aspects of driver behavior, as will be understood by those skilled in the art. Preferably, the headrest adjustment is performed automatically through suitable activation a power adjustable headrest, but the adjustment may alternatively be performed manually by the driver in response to prompts provided by the sensing system in applications where the driver seat is not equipped with a power adjustable headrest.

Figure 1:
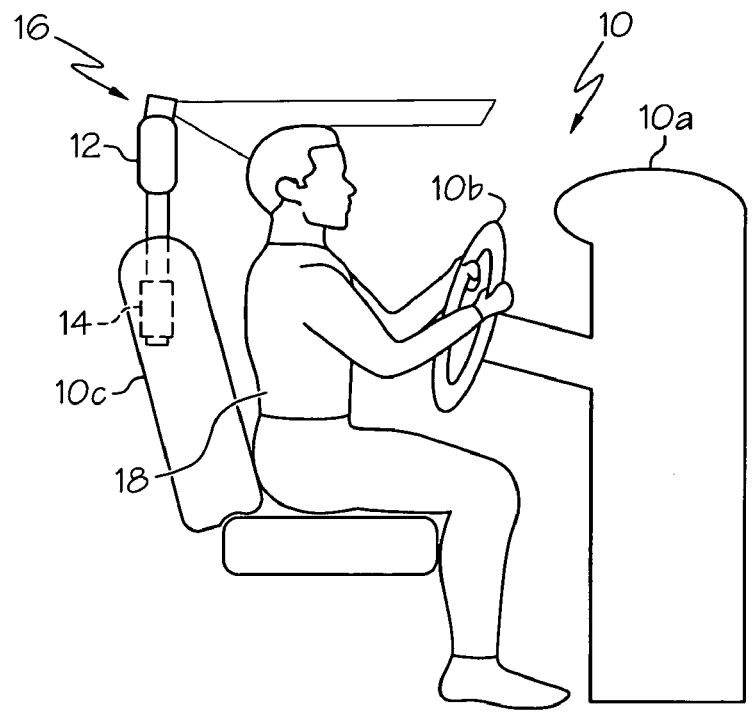
FIG. 1 diagrammatically depicts a vehicle passenger compartment with a driver occupying a seat equipped with an adjustable headrest and a headrest-mounted relative motion sensing system.

Referring to FIG. 1, the reference numeral 10 generally designates a motor vehicle passenger compartment including an instrument panel 10a, a steering wheel 10b and a driver seat 10c. The driver seat 10c is equipped with a power adjustable headrest 12 as signified by the headrest position control mechanism 14, and a relative motion sensing system 16 is mounted on the headrest 12. The vehicle driver 18 is supported by the seat 10c, and the sensing system 16 responds to detected driver head motion to activate control mechanism 14 for suitably adjusting the position of headrest 12 and to assess the driver head pose. In the illustrated embodiment, the control mechanism 14 is configured to primarily adjust the height of headrest 12 relative to seat 10c, but could alternately be configured to additionally adjust the fore/aft position of headrest 12 if desired. Also, the control mechanism 14 can be located in the headrest 12 instead of seat 10c if desired.

Figure 2:
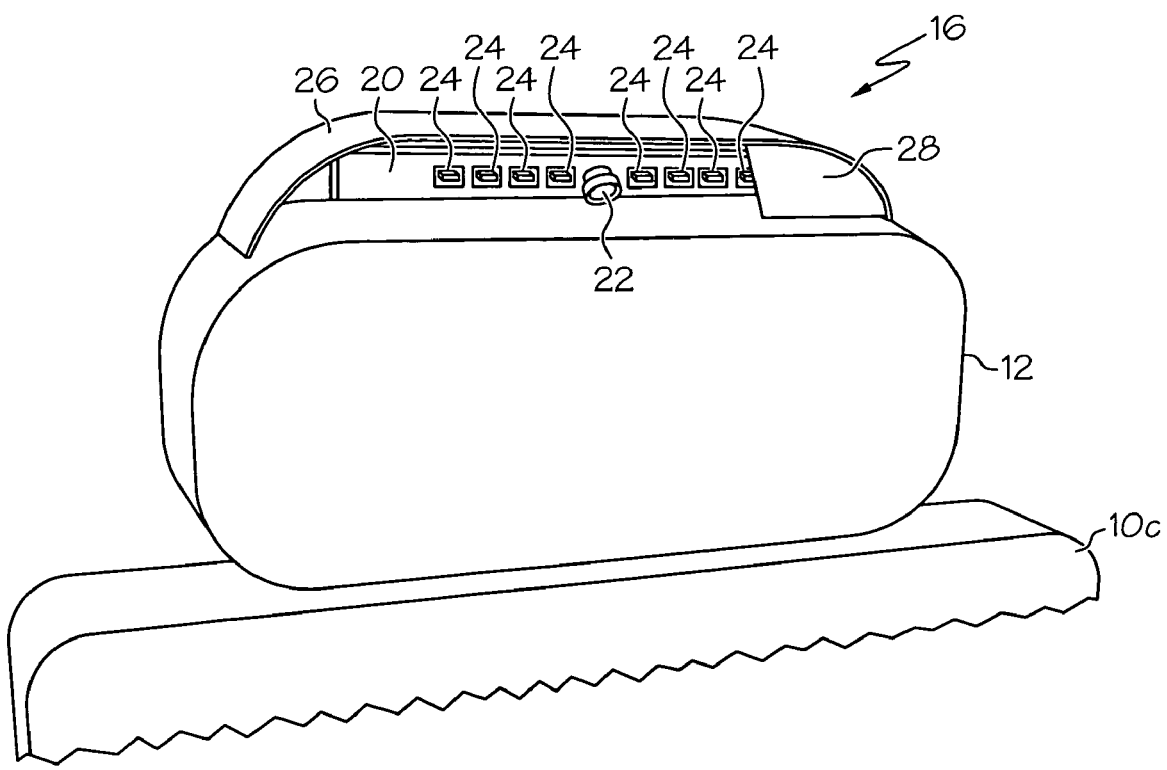
FIG. 2 is an isometric diagram of the headrest and relative motion sensing system of FIG. 1.

FIG. 2 illustrates a preferred mechanization in which the sensing system 16 is mounted in a housing affixed to the top of headrest 12. The housing includes a mounting plate 20 through which a sensor lens 22 and a plurality of infrared light emitting diode (LED) lamps 24 protrude, a shroud 26 for shielding the lens 22 from stray ambient light, and a light-transmissive bezel 28 (only a portion of which is depicted in FIG. 2) for covering and protecting the lens 22 and lamps 24. While the number of lamps 24 and their intensity may vary depending on sensor sensitivity and other factors, it is important that they adequately illuminate the posterior portion of the driver's head during both daytime and nighttime driving.

As explained below, sensing system 16 includes a optical relative motion sensor similar to the sensor used in an optical mouse for a personal computer. Sensors of this type are produced and sold by Agilent Technologies, Inc., for example, and include an imager chip and a digital signal processor programmed to recognize movement of imaged patterns and output Cartesian position coordinates based on the detected movement. The required data acquisition rate of the sensor depends on the application, and we have found that a standard data acquisition rate such as 30 frames/second is sufficient to detect driver head motion. While this type of sensor inexpensive, and therefore particularly advantageous for automotive applications, it only senses changes in the position of the driver's head with respect to the headrest 12. In other words, the position of the driver's head is inferred with respect to an initial position that is assumed instead of sensed.

The head pose of a driver during vehicle operation can be inferred based on sensed head pose characteristics that are common to virtually all drivers during vehicle operation. For example, the head pose of a driver that is operating a vehicle is predominantly forward-looking, and it can be inferred that the head pose is substantially forward-looking when there is a prolonged absence of driver head movement. Furthermore, empirical data reveals that when a driver glances away from the forward direction, the duration of the glance is usually less than two seconds, and almost never more than four seconds. Consequently, the driver's head pose can be periodically inferred as forward-looking based on sensed head pose movement because relatively long duration periods of little or no movement are only characteristic of the forward-looking head pose.

The present invention recognizes that the relative motion information provided by sensing system 16 can additionally be used to accurately position headrest 12, and therefore sensing system 16, with respect to the driver's head. Specifically, the sensor information is used to position the headrest 12 for optimal driver safety and the sensing system 16 is configured to provide optimal sensitivity to driver head motion when the headrest 12 is so positioned.

Figure 3:
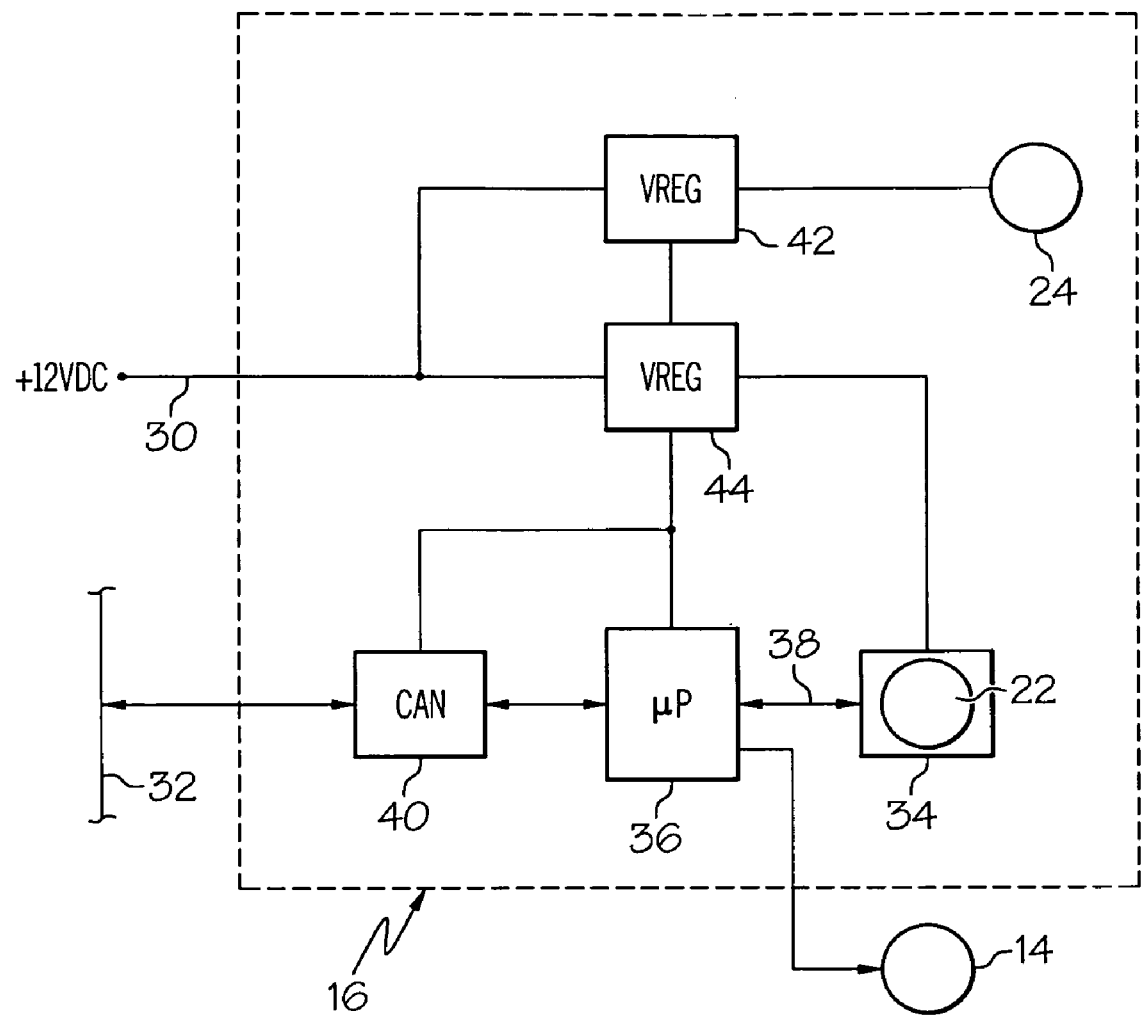
FIG. 3 is a system block diagram of the sensing system of FIGS. 1-2, including a processor for controlling headrest adjustment and assessing driver head pose.

FIG. 3 is a block diagram of the sensing system 16. Referring to FIG. 3, a vehicle power cable 30 supplies 12 VDC to the sensing apparatus 16, and the sensing apparatus 16 communicates with other electronic modules of the vehicle over a vehicle communications bus 32. Reference numeral 34 designates a relative motion optical sensor (with lens 22) such as the Model No. 3080 optical mouse sensor produced and sold by Agilent Technologies, Inc., and reference numeral 36 designates an automotive-grade microprocessor (µP) or digital signal processor. Cartesian coordinate data produced by optical sensor 34 is supplied to an input port of processor 36 via serial peripheral interface (SPI) 38, and processor 36 communicates with the vehicle bus 32 via CAN transceiver 40. A 9V power supply 42 provides operating power to the IR LED lamps 24, and a 3V power supply 44 provides operating power to optical sensor 34, processor 36 and CAN transceiver 40. Processor 36 processes the lateral coordinate data produced by optical sensor 34 to infer the location of the driver's head and its pose. The head location information is used to properly adjust headrest position using the position control mechanism 14, and the head pose information is supplied to other electronic modules of the vehicle via CAN transceiver 40 and communications bus 32. For example, the head pose information can be used to issue a driver alert in the case of an inattentive driver or to belay collision-avoidance warnings in the case of an attentive driver.

Figure 4:
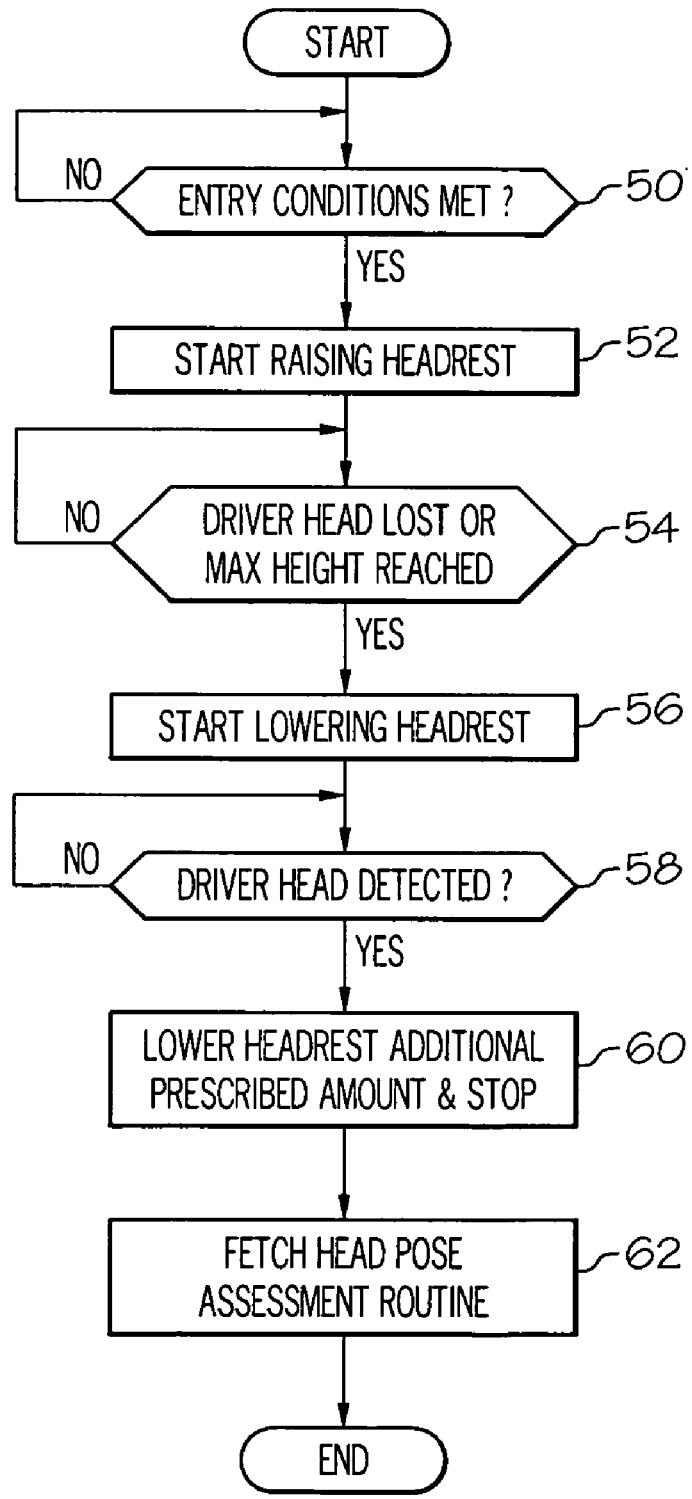
FIG. 4 is a flow diagram representing a software routine carried out by the processor of FIG. 3 for controlling headrest adjustment.
Figure 5:
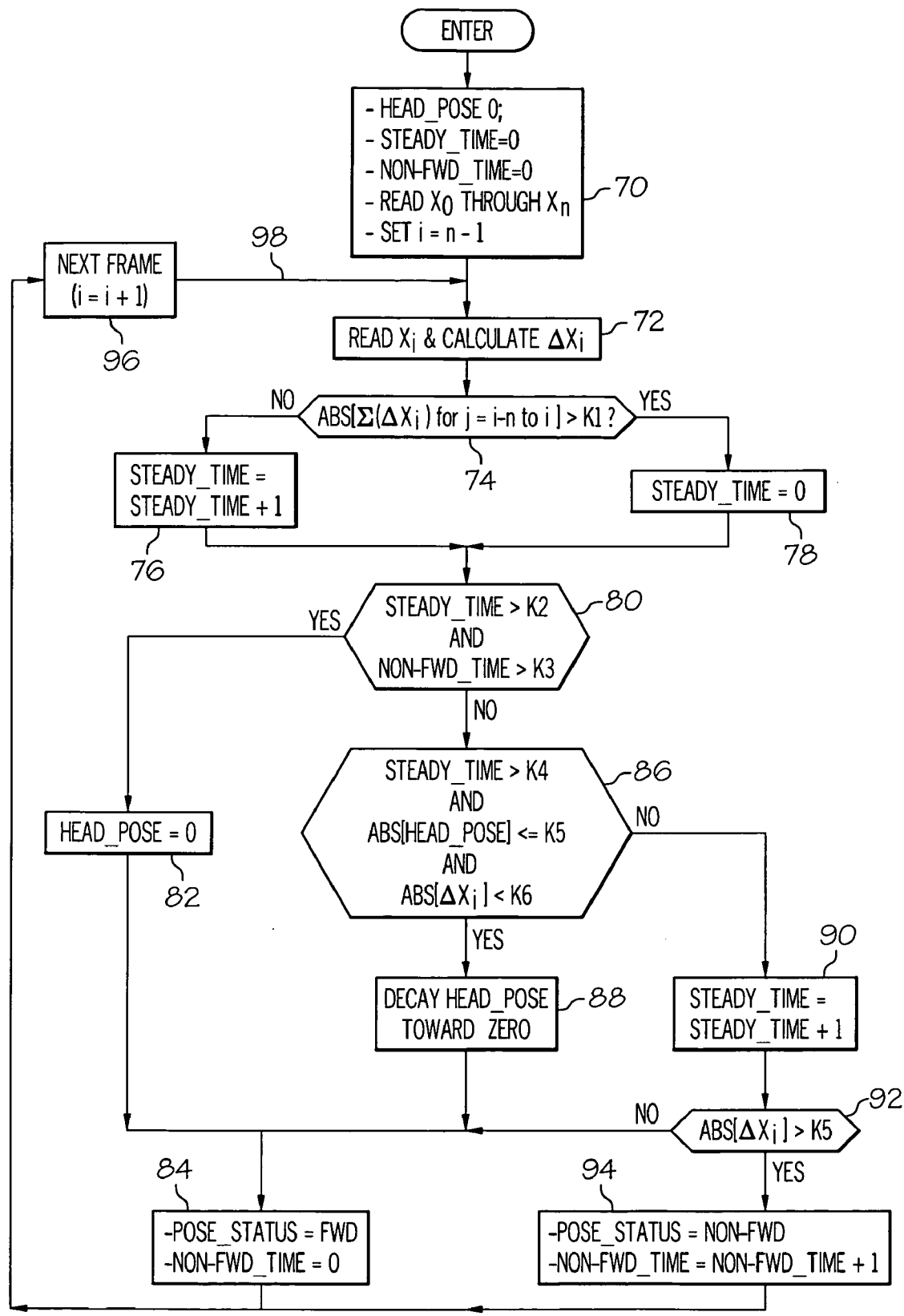
FIG. 5 is a flow diagram representing a software routine carried out by the processor of FIG. 3 for assessing driver head pose.

The flow diagrams of FIGS. 4 and 5 represent software routines executed by the processor 36 of FIG. 3. The flow diagram of FIG. 4 pertains to the positioning of headrest 12, and the flow diagram of FIG. 5 pertains to the assessment of driver head pose.

A software routine corresponding to the flow diagram of FIG. 4 is executed each time the vehicle ignition switch transitions from off to on, and thereafter if conditions indicative of a change in drivers are sensed. Block 50 is first executed to determine if specified entry conditions for headrest adjustment are met. The entry conditions may include, for example, detection of a seat occupant and lack of significant occupant movement. Once the conditions are met, the block 52 and 54 are executed to activate position control mechanism 14 for raising headrest 12 while monitoring the output of sensor 34 to detect a disappearance of the driver's head. When the sensor output indicates that the driver's head has disappeared from view, or if the headrest 12 has been adjusted to its maximum height, blocks 56 and 58 are executed to activate position control mechanism 14 for lowering headrest 12 while monitoring the output of sensor 34 to detect re-appearance of the driver's head. Once the driver's head has been detected, block 60 is executed to continue activation of position control mechanism 14 for lowering headrest 12 by an additional amount to position it for optimal driver safety. In system mechanizations where the position control mechanism 14 is additionally configured to adjust the fore/aft position of the headrest 12, the distance between sensor system 16 and the driver's head can be inferred using sensor 34 because its optical metrics (e.g., summation of pixels and image quality) are highly correlated with proximity. Alternately, the distance between the headrest 12 and the driver's head can be sensed with an additional headrest mounted sensor such as an inexpensive capacitive or ultrasonic proximity sensor. Once the distance is known, the processor 36 activates position control mechanism 14 to correctly position headrest 12 with respect to the driver's head, again to optimize both occupant safety and sensor sensitivity. With the headrest 12 properly positioned, block 62 is executed to fetch the head pose assessment routine.

A software routine corresponding to the flow diagram of FIG. 5 is executed when directed by block 62 of FIG. 4. Referring to FIG. 5, the block 70 designates a series of initialization instructions for resetting a number of parameters to zero and reading an initial series of lateral head pose coordinates produced by optical sensor 34. The parameters reset to zero include the apparent head pose direction HEAD_POSE, a first timer variable STEADY_TIME representing the number of successive sensor frames for which there has been no substantial head movement, and a second timer variable NON-FWD_TIME representing the number of successive sensor frames for which the POSE_STATUS is non-forward. In the case of HEAD_POSE, a zero value indicates a head pose in which the driver's concentration is focused on the forward center field-of-view. The initial lateral head pose coordinates are designated as $X_0$ through $X_n$, where n is an integer having a value of four, for example. A frame index variable i for identifying subsequently acquired lateral coordinate data is initialized to a value of (n+1).

Following initialization, the block 72 reads the lateral head pose coordinate for sensor frame i (that is, $X_i$) and determines the change in value from the previous frame (that is, $X_i - X_{i-1}$, or $\Delta X_i$). The term $\Delta X_i$ thus represents the lateral head movement between the current and previous frames of optical sensor 34. Block 74 sums the head movements over a series of (n+1) frames and compares the absolute value of the sum to a calibrated threshold K1 such as 10. If the absolute value of the sum is less than or equal to K1, the driver head pose is considered to be steady, and the timer variable STEADY_TIME is incremented by block 76. If the absolute value of the sum exceeds K1, there is significant driver head movement, and block 78 resets STEADY_TIME to zero.

Block 80 tests for a condition where there is little or no head movement and POSE_STATUS has been non-forward (NON-FWD) for a prolonged interval. Specifically, block 80 determines if: (1) STEADY_TIME exceeds a calibrated number K2 of sensor frames corresponding to two seconds, for example; and (2) NON-FWD_TIME exceeds a calibrated number K3 of frames corresponding to three seconds, for example. In other words, the condition is detected when the apparent head pose direction has been non-forward for an unreasonably long interval, and there is also generally steady head movement that is characteristic of a forward-looking head pose. When this condition is detected, the routine concludes that the driver's head pose is in fact forward-looking, and blocks 82 and 84 are executed to reset both HEAD_POSE and NON-FWD_TIME to zero, and to set POSE_STATUS to FWD. If the condition tested by block 80 is not present, the block 86 tests for a condition where there is little or no current head movement and the apparent head pose direction is generally forward-looking. Specifically, block 86 determines if: (1) STEADY_TIME exceeds a calibrated number K2 of frames corresponding to one-third second, for example; (2) ABS[HEAD_POSE] is less than or equal to a calibrated displacement K5 from forward (corresponding to a head pose angle of ±20°, for example); and (3) ABS[$\Delta$XI] is less than a calibrated small head movement K6. When this condition is detected, the routine concludes that the driver's head pose is generally forward-looking, and blocks 88 and 84 are executed to decay the apparent head pose direction HEAD_POSE toward zero, to set POSE_STATUS to FWD, and to reset NON-FWD_TIME to zero. The term HEAD_POSE can be decayed, for example, by decrementing positive values of HEAD_POSE and incrementing negative values of HEAD_POSE. If neither of the conditions tested by blocks 80 and 86 are present, the blocks 90 and 92 are executed to update the apparent head pose direction HEAD_POSE based on the value of $\Delta X_i$ determined at block 72, and to compare the updated HEAD_POSE to the calibrated reference value K5. If HEAD_POSE is less than or equal to K5, the apparent head pose direction is generally forward-looking, and block 94 is executed to set POSE_STATUS to FWD and to reset NON-FWD_TIME to zero. On the other hand, if HEAD_POSE is greater than K5, the apparent head pose direction is considered to be non-forward-looking, and block 84 is executed to set POSE_STATUS to NON-FWD and to increment the timer variable NON-FWD_TIME. Each time blocks 84 or 94 are executed to update POSE_STATUS, the routine waits for the coordinate data corresponding to the next frame of optical sensor 34 as indicated at block 96, and then repeats the execution of blocks 72-94 as indicated by flow diagram line 98. Block 96 also updates the frame index variable i for the next frame.

In summary, using a single headrest-mounted relative motion sensor for both driver head pose assessment and headrest adjustment according to this invention reduces system cost and enhances both driver safety and head pose assessment. Driver safety is enhanced by properly positioning the headrest 12, and head pose assessment is enhanced by ensuring optimal sensitivity of the relative motion sensor, regardless of the driver head height. While the present invention has been described with respect to the illustrated embodiment, it is recognized that numerous modifications and variations in addition to those mentioned herein will occur to those skilled in the art. For example, the headrest 12 can be adjusted to its maximum height when the ignition switch transitions from on to off, the sensing system 16 can be variously mounted on or in headrest 12, and so on. Accordingly, it is intended that the invention not be limited to the disclosed embodiment, but that it have the full scope permitted by the language of the following claims.

The invention claimed is:

1. Apparatus for assessing a head pose of a driver supported on a vehicle seat including an adjustable headrest, comprising:
   a relative motion sensor mounted on said headrest for sensing a posterior portion of the driver's head and producing a signal responsive to motion of the posterior portion of the driver's head; and
   a processor for processing the signal produced by the relative motion sensor for controlling adjustment of the headrest to provide both optimal driver safety and optimal sensitivity of the relative motion sensor when determining motion of the posterior portion, and assessing whether the driver's head pose is forward or non-forward with respect to a vehicle frame of reference, wherein the processor assesses the driver's head pose as forward when the motion of the posterior portion is less than a first threshold, a steady head pose condition exists for a period of time that exceeds a second threshold, and a non-forward head pose condition exists for a period of time that exceeds a third threshold.

2. The apparatus of claim 1, where:
   the relative motion sensor is an optical sensor, and optical metrics provided by the relative motion sensor are used to infer a proximity of the headrest to the driver's head.

3. A method of assessing a head pose of a driver supported on a vehicle seat including an adjustable headrest, comprising the steps of:
   providing a relative motion sensor on said headrest for sensing a posterior portion of the driver's head and producing a signal responsive to motion of the posterior portion of the driver's head;
   processing the signal produced by the relative motion sensor for controlling adjustment of the headrest to provide both optimal driver safety and optimal sensitivity of the relative motion sensor when determining motion of the posterior portion; and
   processing the signal produced by the relative motion sensor for assessing whether the driver's head pose is forward or non-forward with respect to a vehicle frame of reference, wherein the driver's head pose is assessed as forward when the motion of the posterior portion is less than a first threshold, a steady head pose condition exists for a period of time that exceeds a second threshold, and a non-forward head pose condition exists for a period of time that exceeds a third threshold.

4. The method of claim 3, where the step of processing the signal produced by the relative motion sensor for controlling adjustment of the headrest includes the steps of:
   raising the headrest to a position where the relative motion sensor cannot sense the driver's head;
   lowering the headrest until the relative motion sensor senses the driver's head; and
   lowering the headrest an additional prescribed amount.

5. The method of claim 4, including the step of:
   orienting the relative motion sensor on the headrest so that optimal sensitivity of the relative motion sensor occurs when the headrest has been lowered the additional prescribed amount.

6. The method of claim 3, including the steps of:
   sensing a proximity of the headrest to the driver's head; and
   adjusting a fore/aft position of the headrest to properly position the headrest with respect to the driver's head.

7. The method of claim 6, where:
the relative motion sensor is an optical sensor, and the proximity of the headrest to the driver's head is inferred from optical metrics provided by the relative motion sensor.

8. The method of claim 4, where the step of raising the headrest to a position where the relative motion sensor cannot sense the driver's head includes the steps of:

raising the headrest while monitoring the signal produced by the relative motion sensor; and discontinuing the raising of the headrest when the relative motion sensor cannot sense the driver's head or the headrest has been raised to a maximum height.

* * * * *